(12) United States Patent
Liang et al.

(10) Patent No.: US 12,727,806 B2
(45) Date of Patent: Sep. 8, 2026

(54) FLEXIBLE ELECTRONIC DEVICE

(71) Applicant: Industrial Technology Research Institute, Hsinchu (TW)

(72) Inventors: Min-Hsiung Liang, Hsinchu County (TW); Chien-Hsun Chu, Hsinchu County (TW); Kuan-Chu Wu, Hsinchu County (TW); Wan-Chen Yang, New Taipei City (TW); Jui-Chang Chuang, Kaohsiung City (TW); Chen-Tsai Yang, Taoyuan City (TW); Heng-Yin Chen, Hsinchu City (TW); Hung-Hsien Ko, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 337 days.

(21) Appl. No.: 18/420,789

(22) Filed: Jan. 24, 2024

(65) Prior Publication Data

US 2024/0341653 A1 Oct. 17, 2024

Related U.S. Application Data

(60) Provisional application No. 63/459,266, filed on Apr. 14, 2023.

(30) Foreign Application Priority Data

Nov. 14, 2023 (TW) ................................ 112143807

(51) Int. Cl.
*A61B 5/263* (2021.01)

(52) U.S. Cl.
CPC ........ *A61B 5/263* (2021.01); *A61B 2562/164* (2013.01); *A61B 2562/18* (2013.01)

(58) Field of Classification Search
CPC ............. A61B 5/263; A61B 2562/164; A61B 2562/18
(Continued)

(56) References Cited

U.S. PATENT DOCUMENTS 10,098,225 B2 10/2018 Chang et al.
10,276,761 B2 4/2019 Huang et al.
(Continued)

FOREIGN PATENT DOCUMENTS

CN 114577372 6/2022
CN 115923914 4/2023
(Continued)

OTHER PUBLICATIONS

"Office Action of Taiwan Counterpart Application", issued on Jun. 17, 2024, p. 1-p. 4.

*Primary Examiner* — Tremesha W Burns
(74) *Attorney, Agent, or Firm* — JCIPRNET

(57) ABSTRACT

A flexible electronic device includes a first encapsulation layer and a sensing structure. The sensing structure is disposed on the first encapsulation layer and includes a substrate, a plurality of first sensing layer, a plurality of second sensing layer, a first groove and a second groove. The substrate includes a main body, a plurality of first branches and a plurality of second branches. The main body has a first side and a second side opposite to each other. The first branches connect the first side. The second branches connect the second side. The first sensing layers are disposed on the first branches. The second sensing layers are disposed on the second branches. The first groove is disposed between the first branches. The second groove is disposed between the second branches.

6 Claims, 10 Drawing Sheets

(58) Field of Classification Search
USPC .......................................................... 174/254
See application file for complete search history.

(56) References Cited

U.S. PATENT DOCUMENTS

| | | | |
|---|---|---|---|
| 2019/0006743 | A1 | 1/2019 | Kirino et al. |
| 2019/0098775 | A1 | 3/2019 | Cho |

FOREIGN PATENT DOCUMENTS

| | | |
|---|---|---|
| TW | M481704 | 7/2014 |
| TW | 202308475 | 2/2023 |

FLEXIBLE ELECTRONIC DEVICE

CROSS-REFERENCE TO RELATED APPLICATION

This application claims the priority benefit of U.S. Provisional Application No. 63/459,266, filed on Apr. 14, 2023 and Taiwan Application No. 112143807, filed on Nov. 14, 2023. The entirety of each of the above-mentioned patent applications is hereby incorporated by reference herein and made a part of this specification.

TECHNICAL FIELD

The present disclosure relates to an electronic device, and also relates to a flexible electronic device.

BACKGROUND

Generally speaking, when disposing or using a flexible electronic device, such as disposing a steering wheel cover or controlling a grip containing electronic components, or disposing or wearing a wearable device containing electronic components (such as knee pads, smart fabrics, etc.), the electronic components in flexible electronic devices are very likely to be damaged or malfunctioned due to deformation problems such as stretching, twisting or bending, which affecting the service life, yield or reliability of flexible electronic devices.

In addition, when the signal transmission element (such as a sensing element) in a flexible electronic device is covered by fabric or leather and a coupling method (or non-direct contact method) is adopted for signal transmission, since the signal needs to pass through fabric or leather, signal abnormality problems such as poor signal transmission or bad reception occurs very often.

SUMMARY

Embodiments of the present disclosure provide a flexible electronic device that may alleviate the problems of poor service life, yield or reliability caused by deformation (such as stretching, twisting or bending), or may improve signal transmission or reception.

A flexible electronic device according to an embodiment of the present disclosure includes a first encapsulation layer and a sensing structure. The sensing structure is disposed on the first encapsulation layer and includes a substrate, a plurality of first sensing layers, a plurality of second sensing layers, a first groove and a second groove. The substrate includes a main body, a plurality of first branches and a plurality of second branches. The main body has a first side and a second side opposite to each other. A plurality of first branches connect the first side. A plurality of second branches connect the second side. A plurality of first sensing layers are disposed on the plurality of first branches. A plurality of second sensing layers are disposed on the plurality of second branches. The first groove is disposed between the plurality of first branches. The second groove is disposed between the plurality of second branches.

A flexible electronic device according to an embodiment of the present disclosure includes a first encapsulation layer, a sensing structure, a second encapsulation layer and a signal amplification layer. The sensing structure is disposed on the first encapsulation layer and includes a substrate and a sensing layer disposed on the substrate. The second encapsulation layer is disposed on the sensing layer. The signal amplification layer is embedded in the second encapsulation layer. The signal amplification layer overlaps the sensing layer in the normal direction of the substrate.

A flexible electronic device according to an embodiment of the present disclosure includes a first encapsulation layer and a sensing structure. The first encapsulation layer includes a first region, a second region and a third region. The first region has a concave recessed in the first encapsulation layer. The second region has an opening extending through the first encapsulation layer. The third region has a cavity embedded in the first encapsulation layer. The sensing structure is disposed on the first encapsulation layer and includes a substrate and a sensing layer. The substrate is disposed in the concave. The sensing layer is disposed in the concave and on the substrate.

In order to make the present disclosure more obvious and easy to understand, embodiments are specifically cited below, and are described in detail below with reference to the accompanying drawings.

DETAILED DESCRIPTION OF DISCLOSED EMBODIMENTS

Figure 1:
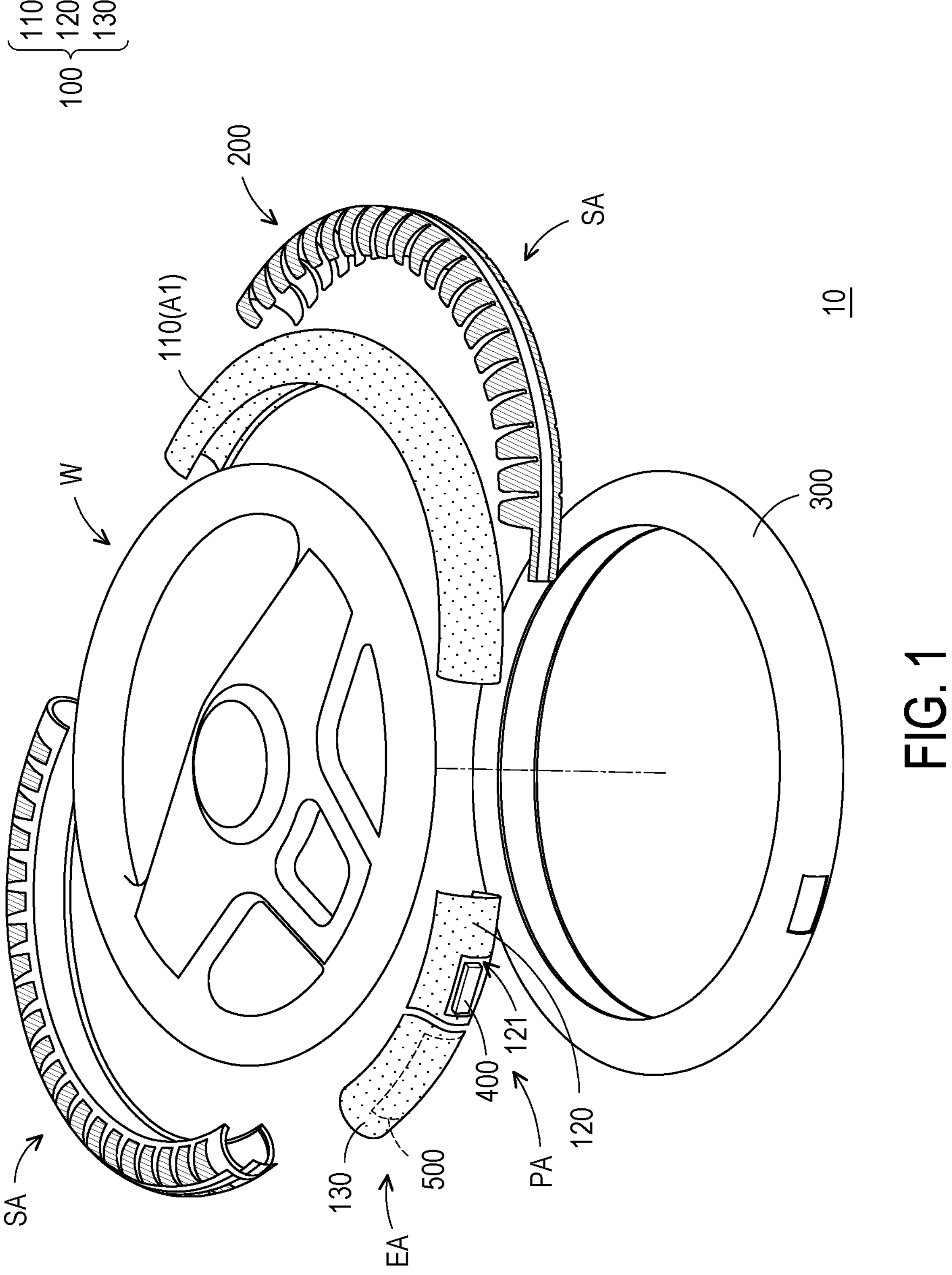
FIG. 1 is a schematic exploded view of a flexible electronic device according to an embodiment of the present disclosure.
Figures 2A, 2B, 2C:
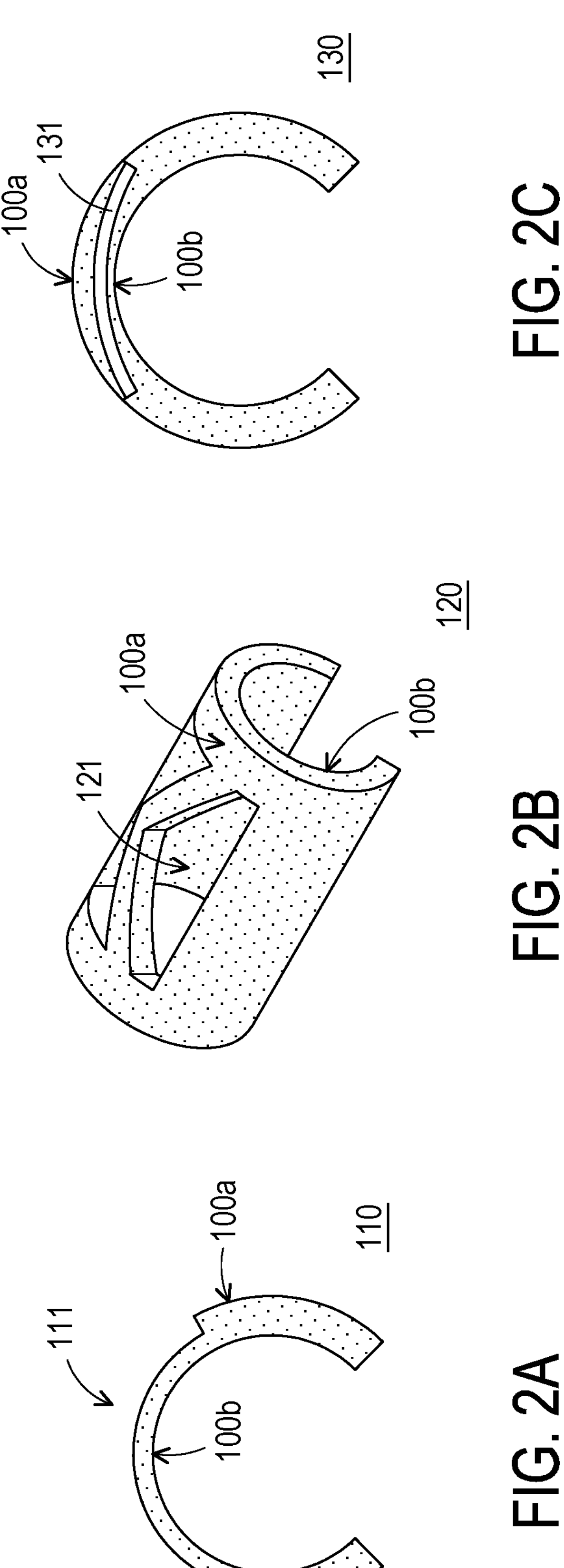
FIG. 2A is a schematic cross-sectional view of the first encapsulation layer in the sensing area of the flexible electronic device in FIG. 1.
FIG. 2B is a schematic perspective view of the first encapsulation layer in the power supply area of the flexible electronic device in FIG. 1.
FIG. 2C is a schematic cross-sectional view of the first encapsulation layer in the electronic component area of the flexible electronic device in FIG. 1.
Figures 3A, 3B:
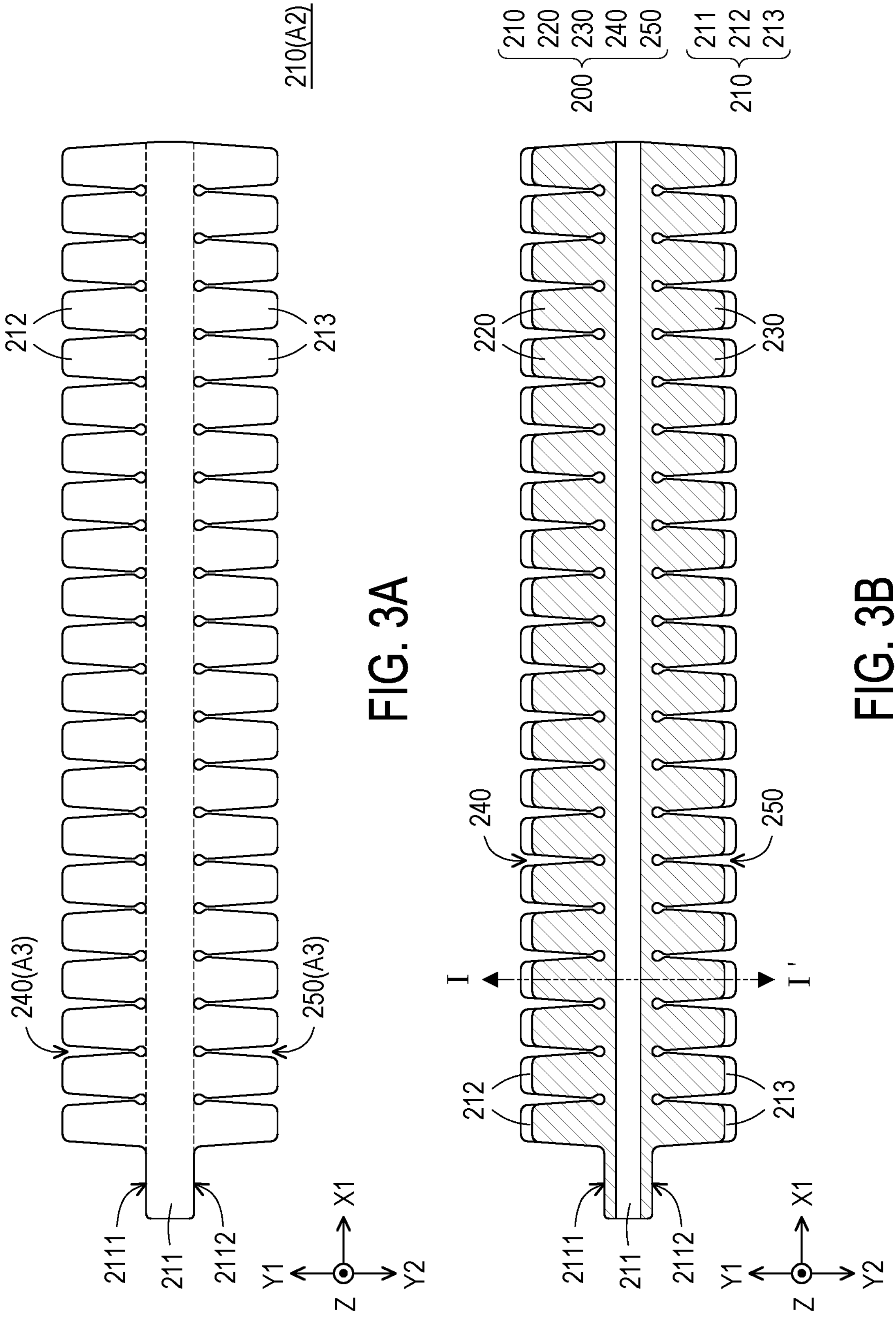
FIG. 3A is a schematic expanded view of the substrate of the sensing area of the flexible electronic device in FIG. 1.
FIG. 3B is a schematic expanded view of the sensing area of the flexible electronic device in FIG. 1.
Figure 3C:
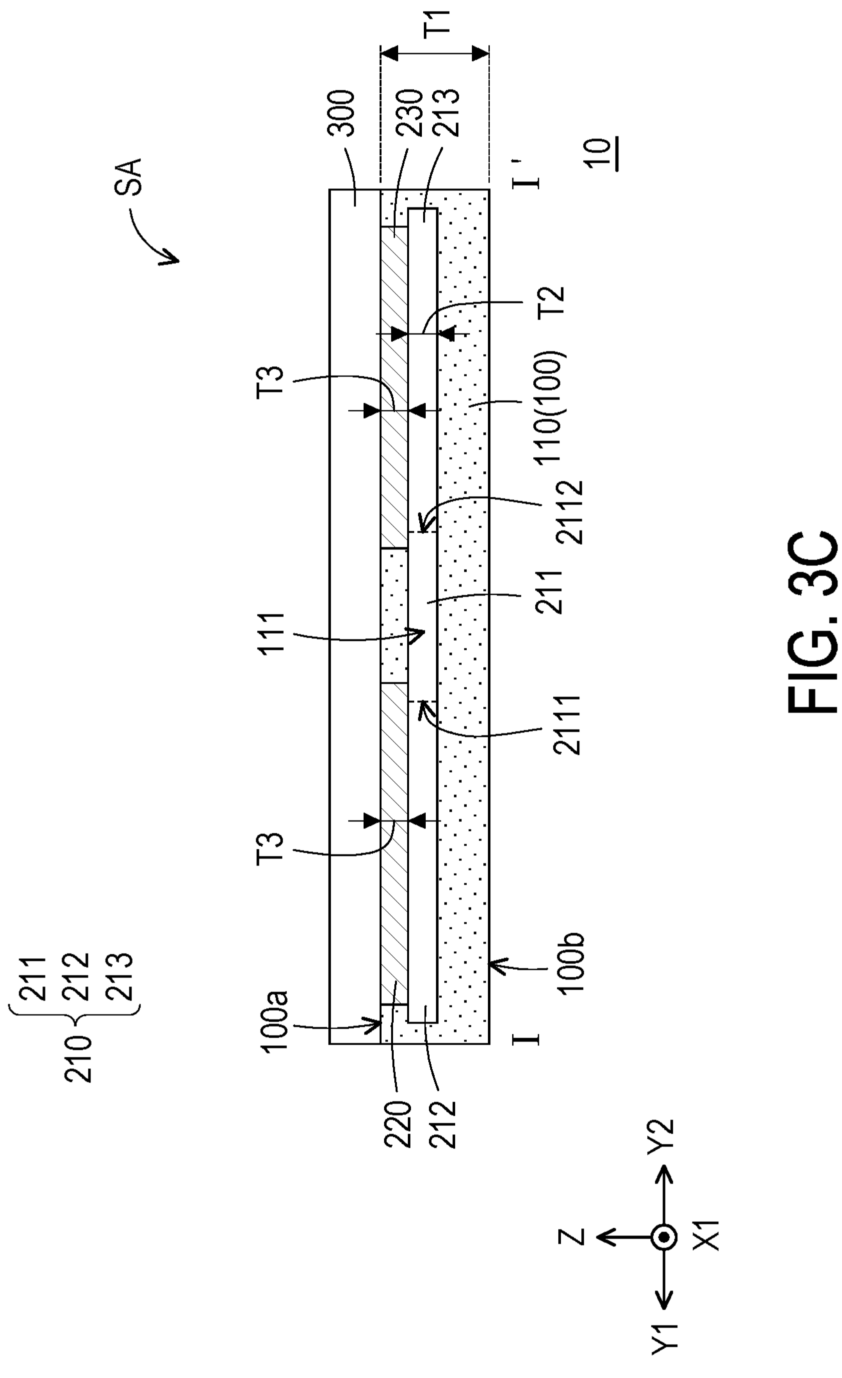
FIG. 3C is a schematic cross-sectional view of the flexible electronic device of FIG. 3B taken along the line I-I'.

FIG. 1 is a schematic exploded view of a flexible electronic device according to an embodiment of the present disclosure. FIG. 2A is a schematic cross-sectional view of the first encapsulation layer in the sensing area of the flexible electronic device in FIG. 1. FIG. 2B is a schematic perspective view of the first encapsulation layer in the power supply area of the flexible electronic device in FIG. 1. FIG. 2C is a schematic cross-sectional view of the first encapsulation layer in the electronic component area of the flexible electronic device in FIG. 1. FIG. 3A is a schematic expanded view of the substrate of the sensing area of the flexible electronic device in FIG. 1. FIG. 3B is a schematic expanded view of the sensing area of the flexible electronic device in FIG. 1. FIG. 3C is a schematic cross-sectional view of the flexible electronic device of FIG. 3B taken along the line I-I'. For clarity of the drawings and convenience of description, some elements in the flexible electronic device are omitted from FIG. 1, FIG. 2A to FIG. 2C, and FIG. 3A to FIG. 3B.

Please refer to FIG. 1, FIG. 2A to FIG. 2C, and FIG. 3A to FIG. 3B. The flexible electronic device 10 in this embodiment may be, for example, a steering wheel cover applied to the steering wheel W, but the disclosure is not limited thereto. The flexible electronic device 10 of this embodiment has a sensing area SA, a power supply area PA and an electronic component area EA. The flexible electronic device 10 of this embodiment may include a first encapsulation layer 100, a sensing structure 200, a second encapsulation layer 300, a power supply device 400 and a system component 500.

Specifically, the first encapsulation layer 100 includes a first region 110, a second region 120 and a third region 130. The first region 110 is disposed corresponding to the sensing area SA, the second region 120 is disposed corresponding to the power supply area PA, and the third region 130 is disposed corresponding to the electronic component area EA. The first encapsulation layer 100 has a first surface 100*a* and a second surface 100*b* opposite to each other. As shown in FIG. 2A and FIG. 3C, the first region 110 has a concave 111 recessed in the first surface 100*a* of the first encapsulation layer 100. As shown in FIG. 2B, the second region 120 has an opening 121 penetrating the first encapsulation layer 100, and the opening 121 may connect the first surface 100*a* and the second surface 100*b*. As shown in FIG. 2C, the third region 130 has a cavity 131 embedded in the first encapsulation layer 100, and the cavity 131 is located between the first surface 100*a* and the second surface 100*b*.

In this embodiment, when the first encapsulation layer 100 is deformed such as stretching, torsion, or bending due to external forces, since the second region 120 has an opening 121 that may penetrate the first encapsulation layer 100, the deformation amount of the second region 120 may be greater than the deformation amount of the first region 110 and the deformation amount of the third region 130. Since the first region 110 has the concave 111 recessed in the first surface 100*a* of the first encapsulation layer 100, the deformation amount of the first region 110 may be greater than the deformation amount of the third region 130. For example, when the deformation amount of the third region 130 is set to 1, the deformation amount of the first region 110 may be, for example, 1.08, and the deformation amount of the second region 120 may be, for example, 3.83 (i.e., the ratio of the deformation amount of the first region 110, the deformation amount of the second region 120 and the deformation amount of the third region 130 may be, for example, 1.08:3.83:1.), but the disclosure is not limited thereto. In some embodiments not shown, the design of the concave 111, the opening 121 and cavity 131 of the first encapsulation layer 100 may also be applied to the second encapsulation layer.

In this embodiment, since the deformation amount of the second region 120 may be greater than the deformation amount of the first region 110 and the deformation amount of the third region 130, when an external force is applied, the external force may be withstand by increasing the deformation amount for a local portion (second region 120), and limiting the deformation amount of the first region 110 and the third region 130 to protect the sensing structure 200 disposed in the first region 110 and the system component 500 disposed in the third region 130.

In this embodiment, the first encapsulation layer 100 has a thickness T1. The material of the first encapsulation layer 100 may include polydimethylsiloxane (PDMS), trimethylsiloxane (—O—$Si(CH_3)_3$), hexamethyldisiloxane (HMDSO), fabric or leather, but the disclosure is not limited thereto.

As shown in FIG. 3A to FIG. 3C, in the sensing area SA, the sensing structure 200 is disposed on the first encapsulation layer 100. The sensing structure 200 includes a substrate 210, a plurality of first sensing layers 220, a plurality of second sensing layers 230, a first groove 240 and a second groove 250. The substrate 210 is disposed on the first encapsulation layer 100, and the substrate 210 is disposed in the concave 111 of the first region 110 of the first encapsulation layer 100. In this embodiment, the substrate 210 has a thickness T2. The material of the substrate 210 may include polyimide (PI), polyethylene (PE), polypropylene (PP), polyvinyl chloride (PVC), polyethylene terephthalate (PET), polystyrene (PS), polycarbonate (PC), foam, etc., but the disclosure is not limited thereto. The substrate 210 may be a printed circuit board (PCB) or a flexible printed circuit board (FPCB), but the disclosure is not limited thereto.

In this embodiment, the substrate 210 may include a main body 211, a plurality of first branches 212 and a plurality of second branches 213. The main body 211 has a first side 2111 and a second side 2112 opposite to each other. The plurality of first branches 212 respectively connect the first side 2111, and the plurality of second branches 213 respectively connect the second side 2112. In this embodiment, the plurality of first branches 212 and the plurality of second branches 213 may be arranged symmetrically with respect to the main body 211, but the disclosure is not limited thereto. In some embodiments, the plurality of first branches and the plurality of second branches may also be arranged asymmetrically relative to the main body.

In this embodiment, the extension direction of the first branch 212 is the first extension direction Y1, the extension direction of the second branch 213 is the second extension direction Y2, and the extension direction of the main body 211 is the third extension direction X1. The first extension direction Y1 of the first branch 212 may be substantially parallel to the second extension direction Y2 of the second branch 213, and the third extension direction X1 of the main body 211 may be substantially perpendicular to the first extension direction Y1 and the second extension direction Y1, but the disclosure is not limited thereto. In some embodiments, the main body 211 and the plurality of first branches 212 of the substrate 210 may be arranged in a comb shape, and the main body 211 and the plurality of second branches 213 may also be arranged in a comb shape.

In this embodiment, the first encapsulation layer 100 in the sensing area SA has a first area A1, the substrate 210 in the sensing area SA has a second area A2, and the groove in the sensing area SA (that is, the first groove 240 and the second groove 250) have the third area A3. The second area A2 may be 97% of the first area A1, and the third area A3 may be 3% of the first area A1, but the disclosure is not limited thereto. In some embodiments, the second area A2 may also be 10% to 97% of the first area A1, and the third area A3 may also be 3% to 90% of the first area A1. In some embodiments, the second area A2 may also be the sum of the areas of the main body 211 of the substrate 210, the plurality of first branches 212 and the plurality of second branches 213.

A plurality of first sensing layers 220 and a plurality of second sensing layers 230 are disposed in the concave 111 of the first encapsulation layer 100 and on the substrate 210. The plurality of first sensing layers 220 are disposed on the plurality of first branches 212, and the plurality of second sensing layers 230 are disposed on the plurality of second branches 213. In some embodiments, the plurality of first sensing layers 220 may be disposed in a comb shape corresponding to the first side 2111 of the main body 211 and the plurality of first branches 212, and the plurality of second sensing layers 230 may be disposed in a comb shape corresponding to the second side 2112 of the main body 211 and the plurality of second branches 213, but the disclosure is not limited thereto. In this embodiment, the first sensing layer 220 may be electrically separated from the second sensing layer 230.

In this embodiment, the sensing layer (i.e., the first sensing layer 220 and the second sensing layer 230) has a thickness T3. The thickness T1 of the first encapsulation layer 100 may be, for example, greater than the sum of the thickness T2 of the substrate 210 and the thickness T3 of the sensing layer, whereby the first encapsulation layer 100 may be adopted to define the curvature and appearance of the flexible electronic device 10. In addition, excessive bending and twisting of the sensing structure 200 may be avoided to improve the reliability of the flexible electronic device 10.

In this embodiment, the first sensing layer 220 and the second sensing layer 230 may be adopted to sense physiological signals of the human body, such as electrocardiogramalectromyography (EMG), etc., but the disclosure is not limited thereto. The first sensing layer 220 and the second sensing layer 230 may be sensing electrodes, and the materials of the first sensing layer 220 and the second sensing layer 230 may include copper, titanium, molybdenum, gold, silver, aluminum or a combination of the above, the disclosure is not limited thereto.

In this embodiment, the shapes of the first branch 212, the second branch 213, the first sensing layer 220 and the second sensing layer 230 may be elongated, but the disclosure is not limited thereto. In some embodiments, the shapes of the first branch 212, the second branch 213, the first sensing layer 220 and the second sensing layer 230 may also be trapezoidal, triangular, elliptical, circular or irregular.

In this embodiment, a flexible conductive material is adopted as the sensing layer (i.e., the first sensing layer 220 and the second sensing layer 230), and a flexible encapsulation material is adopted as the encapsulation layer (i.e., the first encapsulation layer 100 and the second encapsulation layer 300). In this way, it is possible to reduce the Young's modulus of the flexible electronic device 10 and reduce the stress generated by the flexible electronic device 10 when the flexible electronic device 10 is deformed such as stretched, twisted or bent. In this embodiment, the Young's modulus of the sensing layer (i.e., the first sensing layer 220 and the second sensing layer 230) may be, for example, 0.05 GPa to 150 GPa, and the Young's modulus of the flexible electronic device 10 may be, for example, 0.05 GPa to 100 GPa, the ratio R1 of the Young's modulus of the sensing layer (i.e., the first sensing layer 220 and the second sensing layer 230) to the Young's modulus of the flexible electronic device 10 may be, for example, 0.0005 to 3000, but the disclosure is not limited thereto. For example, compared to a flexible electronic device with a ratio R1 of 25, a flexible electronic device with a ratio R1 of 12.5 may reduce stress during deformation such as stretching, torsion, or bending.

The first groove 240 is disposed between the plurality of first branches 212, and the second groove 250 is disposed between the plurality of second branches 213. The first groove 240 and the second groove 250 may expose the first encapsulation layer 100. In this embodiment, the first groove 240 and the second groove 250 may be symmetrically arranged relative to the main body 211, but the disclosure is not limited thereto. In this embodiment, the first groove 240 may be regarded as a gap between two adjacent first branches 212 in the plurality of first branches 212, and may be regarded as a gap between two adjacent first sensing layers 220 in the plurality of first sensing layers 220. The second groove 250 may be regarded as the gap between two adjacent second branches 213 in the plurality of second branches 213, and may be regarded as the gap between the two adjacent second sensing layers 230 in the plurality of second sensing layers 230. In this embodiment, the term "adjacent" means that there are no other identical elements between two elements. In some embodiments, the first groove and the second groove may also be arranged asymmetrically relative to the main body.

The second encapsulation layer 300 is disposed on the first sensing layer 220 and the second sensing layer 230. The second encapsulation layer 300 may cover the first encapsulation layer 100. In this embodiment, the material of the second encapsulation layer 300 may include polydimethylsiloxane (PDMS), trimethylsiloxane (—O—Si$(CH_3)_3$), hexamethyldisiloxane (HMDSO), fabric or leather, but the disclosure is not limited thereto. In this embodiment, the second encapsulation layer 300 may be disposed in a manner such as adhesion, adhesive filling or insertion, but is not limited thereto.

As shown in FIG. 1, in the power supply area PA, the power supply device 400 is disposed in the opening 121 of the second region 120 of the first encapsulation layer 100.

As shown in FIG. 1, in the electronic component area EA, the system component 500 is disposed in the cavity 131 of the third region 130 of the first encapsulation layer 100, and the system component 500 may be electrically connected to the sensing layer (i.e., the first sensing layer 220 and the second sensing layer 230). In this embodiment, the system components 500 may include chips (sensing chip and/or system chip), circuits, wireless/wired transmission components, etc., but the disclosure is not limited thereto.

In this embodiment, through the arrangement of the first groove 240 and the second groove 250, the stress generated by the flexible electronic device 10 during deformation such as stretching, twisting or bending may be reduced and the overall amount of stress may be increased, so that the average allowable stretch amount of the flexible electronic device 10 may be increased by more than 20%, and the flexible electronic device 10 may be adapted to deformations such as stretching, twisting or bending to avoid damage or failure during configuration or use, thereby improving the service life, yield or reliability of the flexible electronic device 10. For example, under the same deformation (Ax), compared to a flexible electronic device without a groove, the flexible electronic device 10 of this embodiment may evenly disperse the stress through the configuration of a groove, thereby significantly reducing the stress value by about 13.3 times.

Although the flexible electronic device 10 of this embodiment may be, for example, a steering wheel cover applied to the steering wheel W, the disclosure does not limit the fields which the flexible electronic device 10 may be applied to. In some embodiments, the flexible electronic device 10 may also be applied to bicycle grips, motorcycle grips, fitness equipment grips, walker grips or other control grips. In some embodiments, the flexible electronic device 10 may also be applied to car seats, toilet seats, other seats, or other cushions. In some embodiments, the flexible electronic device may also be applied to wearable handheld devices, mobile phone case devices or smart assistive devices.

Other embodiments will be listed below as illustrations. It must be noted here that the following embodiments follow the component numbers and part of the content of the previous embodiments, where the same numbers are used to represent the same or similar elements, and descriptions of the same technical content are omitted. For descriptions of omitted parts, reference may be made to the foregoing embodiments and will not be repeated in the following embodiments.

Figure 4:
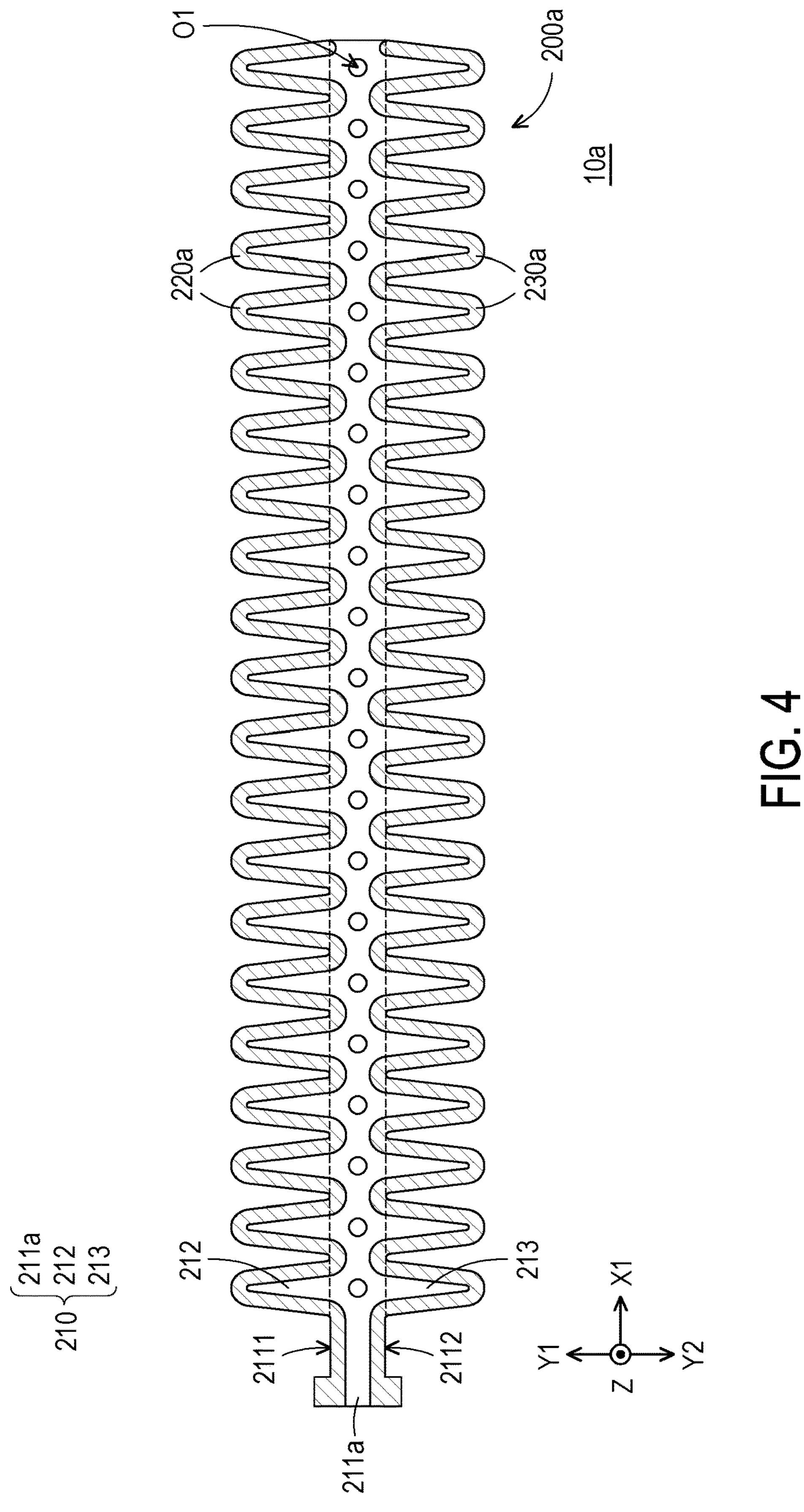
FIG. 4 is a schematic expanded view of the sensing area of a flexible electronic device according to another embodiment of the present disclosure.

FIG. 4 is a schematic expanded view of the sensing area of a flexible electronic device according to another embodiment of the present disclosure. Please refer to FIG. 4 and FIG. 3A both. The flexible electronic device 10*a* of this embodiment is similar to the flexible electronic device 10 in FIG. 3A. The only difference between the two is that in the flexible electronic device 10*a* of this embodiment, the first sensing layer 220*a* of the sensing structure 200*a* does not completely cover the first branch 212, and the second sensing layer 230*a* does not completely cover the second branch 213.

Specifically, please refer to FIG. 4. The plurality of first sensing layers 220*a* may be disposed in a wavy shape corresponding to the edges of the plurality of first branches 212, and the plurality of second sensing layers 230*a* may disposed in a wavy shape corresponding to the edges of the plurality of second branches 213.

In this embodiment, the main body 211*a* of the substrate 210 further has a plurality of openings O1. A plurality of openings O1 are disposed between the first side 2111 and the second side 2112. The plurality of openings O1 may expose the first encapsulation layer 100.

Figure 5:
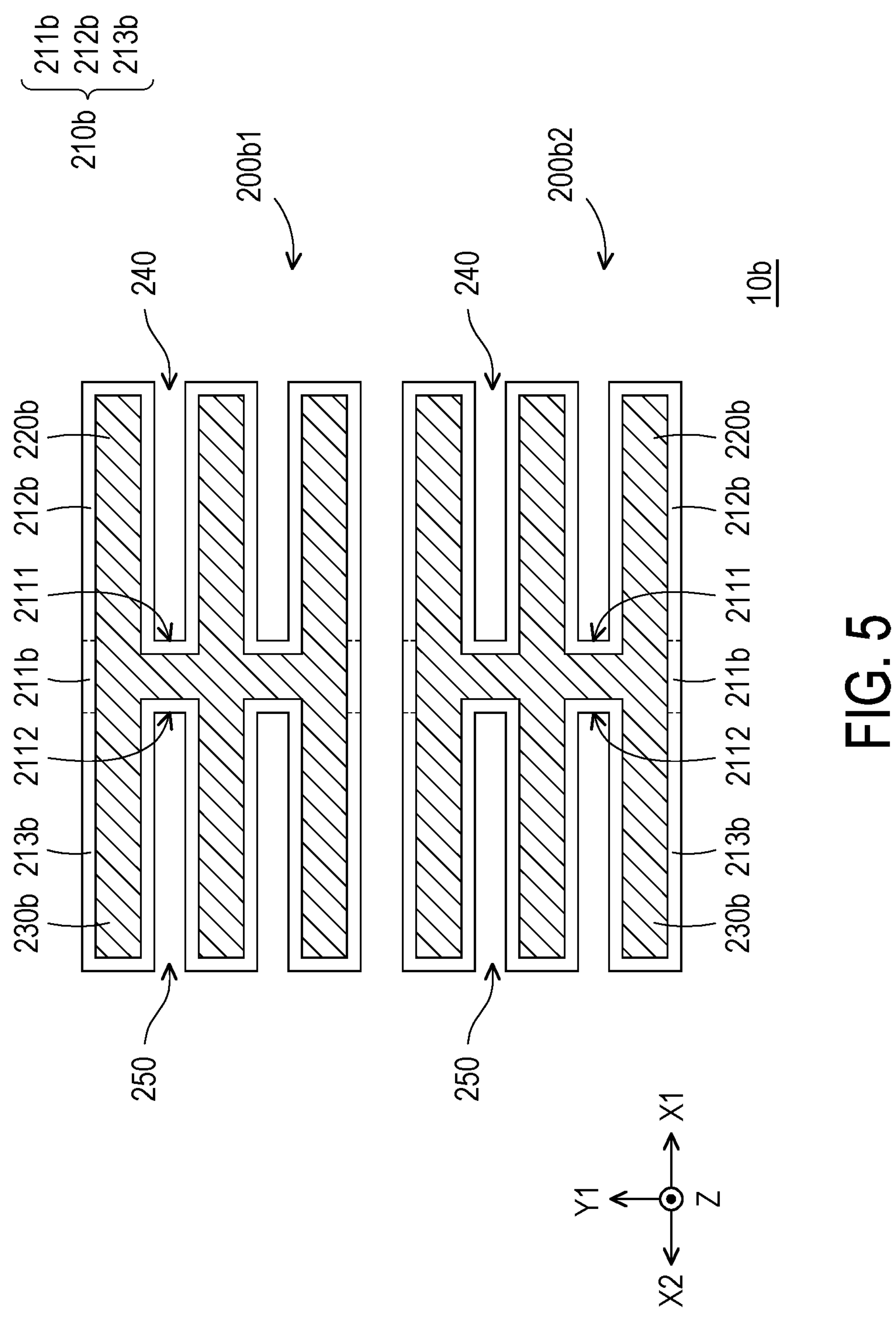
FIG. 5 is a schematic expanded view of a sensing area of a flexible electronic device according to another embodiment of the present disclosure.

FIG. 5 is a schematic expanded view of the sensing area of a flexible electronic device according to another embodiment of the present disclosure. Please refer to FIG. 5 and FIG. 3A both. The flexible electronic device 10*b* of this embodiment is similar to the flexible electronic device 10 in FIG. 3A. The only difference between the two is that the flexible electronic device 10*b* of this embodiment may include a first sensing structure 200*b*1 and the second sensing structure 200*b*2, and the first sensing structure 200*b*1 and the second sensing structure 200*b*2 are electrically separated from each other.

Specifically, please refer to FIG. 5. The substrate 210*b* of the first sensing structure 200*b*1 (or the second sensing structure 200*b*2) may include a main body 211*b*, a plurality of first branches 212*b* and a plurality of second branches 213*b*. The plurality of first branches 212*b* respectively connect the first side 2111 of the main body 211*b*, and the plurality of second branches 213*b* respectively connect the second side 2112 of the main body 211*b*. In this embodiment, the plurality of first branches 212*b* and the plurality of second branches 213*b* may be arranged symmetrically with respect to the main body 211*b*, but the disclosure is not limited thereto. In some embodiments, the plurality of first branches and the plurality of second branches may also be arranged asymmetrically relative to the main body.

The extension direction of the first branch 212*b* is the third extension direction X1, the extension direction of the second branch 213*b* is the fourth extension direction X2, and the extension direction of the main body 211*b* is the first extension direction Y1. The third extension direction X1 of the first branch 212*b* may be substantially parallel to the fourth extension direction X2 of the second branch 213*b*, and the first extension direction Y1 of the main body 211 may be substantially perpendicular to the third extension direction X1 and the fourth extension direction X2, but the disclosure is not limited thereto. In some embodiments, the main body 211*b* and the plurality of first branches 212*b* of the substrate 210*b* may be arranged in a comb shape, and the main body 211*b* and the plurality of second branches 213*b* may also be arranged in a comb shape.

The plurality of first sensing layers 220*b* are disposed on the first side 2111 of the main body 211*b* and the plurality of first branches 212*b* and are arranged in a comb shape, and the plurality of second sensing layers 230*b* are disposed on the second side 2112 of the main body 211*b* and the plurality of second branches 213*b* and are arranged in a comb shape. In this embodiment, the first sensing structure 200*b*1 may be electrically separated from the second sensing structure 200*b*2. The first groove 240 is disposed between the plurality of first branches 212*b*, and the second groove 250 is disposed between the plurality of second branches 213*b*. The first groove 240 and the second groove 250 may expose the first encapsulation layer (not shown). In this embodiment, the first groove 240 and the second groove 250 may be symmetrically arranged relative to the main body 211*b*, but the disclosure is not limited thereto. In this embodiment, the first groove 240 may be regarded as a gap between two adjacent first branches 212*b* in the plurality of first branches 212*b*, and may be regarded as a gap between two adjacent first sensing layers 220*b* in the plurality of first sensing layers 220*b*. The second groove 250 may be regarded as the gap between two adjacent second branches 213*b* in the plurality of second branches 213*b*, and may be regarded as the gap between two adjacent second sensing layers 230*b* in the plurality of second sensing layers 230*b*. In some embodiments, the first groove and the second groove may also be arranged asymmetrically relative to the main body.

Figures 6A, 6B:
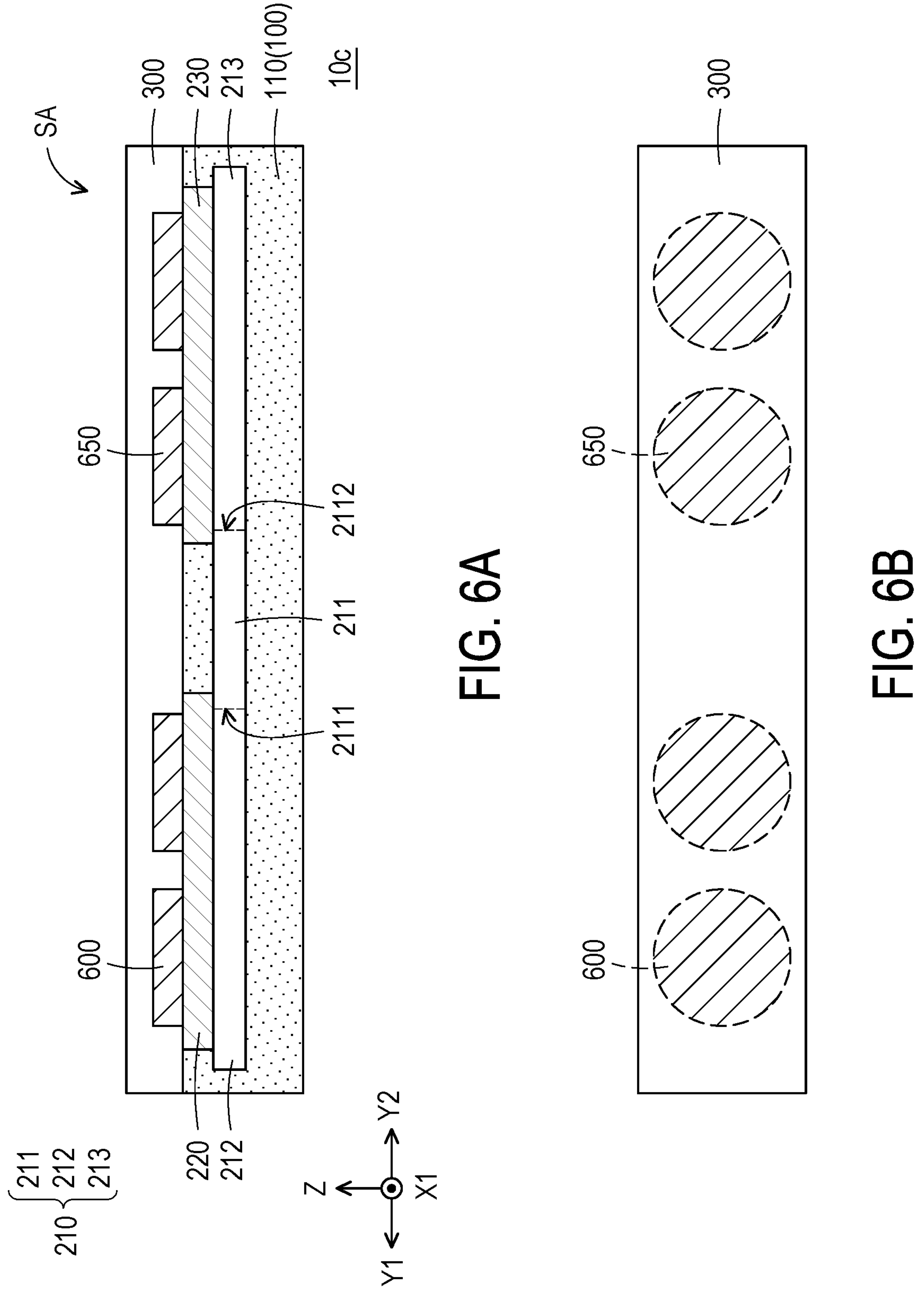
FIG. 6A is a schematic cross-sectional view of a sensing area of a flexible electronic device according to another embodiment of the present disclosure.
FIG. 6B is a schematic top view of the sensing area of the flexible electronic device in FIG. 6A.

FIG. 6A is a schematic cross-sectional view of a sensing area of a flexible electronic device according to another embodiment of the present disclosure. FIG. 6B is a schematic top view of the sensing area of the flexible electronic device in FIG. 6A. For clarity of the drawing and convenience of explanation, some elements in the flexible electronic device are omitted from FIG. 6B. Please refer to FIG. 6A, FIG. 6B and FIG. 3B at the same time. The flexible electronic device 10*c* of this embodiment is similar to the flexible electronic device 10 in FIG. 3B. The only difference between them is that the flexible electronic device 10*c* of this embodiment further includes a signal amplification layer 600 and signal amplification layer 650.

Specifically, please refer to FIG. 6A. The signal amplification layer 600 is disposed on the first sensing layer 220, and the signal amplification layer 600 may be electrically connected to the first sensing layer 220. The signal amplification layer 650 is disposed on the second sensing layer 230, and the signal amplification layer 650 may be electrically connected to the second sensing layer 230. The signal amplification layer 600 and the signal amplification layer 650 may be embedded in the second encapsulation layer 300. The signal amplification layer 600 and the signal amplification layer 650 may respectively overlap the first sensing layer 220 and the second sensing layer 230 in the normal direction Z of the substrate 210. In this embodiment, the materials of the signal amplification layer 600 and the signal amplification layer 650 may include copper, titanium, molybdenum, gold, silver, aluminum or a combination thereof, but the disclosure is not limited thereto.

In this embodiment, through the arrangement of the signal amplification layer 600 and the signal amplification layer 650, the amount of electrical coupling may be increased, thereby increasing the intensity of the signal transmitted or received by the flexible electronic device 10*c*. For example, when the material of the second encapsulation layer 300 is leather, the coupling amount of the flexible electronic device 10*c* of this embodiment is 12.699 pF, whereas the coupling amount of the flexible electronic device without the signal amplification layer is 3.1903 pF. When the material of the second encapsulation layer 300 is porous leather, the coupling amount of the flexible electronic device 10*c* in this embodiment is 19.191 pF, whereas the coupling amount of the flexible electronic device without the signal amplification layer is 3.5178 pF.

Please refer to the top view of FIG. 6B. In this embodiment, the shapes of the signal amplification layer 600 and the signal amplification layer 650 may be circular, but the disclosure is not limited thereto. In some embodiments, the shape of the signal amplification layer may also be a rectangle, a triangle, a rhombus, a pentagon, a hexagon, a mixed triangle (including a triangle with an upper vertex and a triangle with a lower vertex) or a combination of the above, but the disclosure is not limited thereto.

Figure 7:
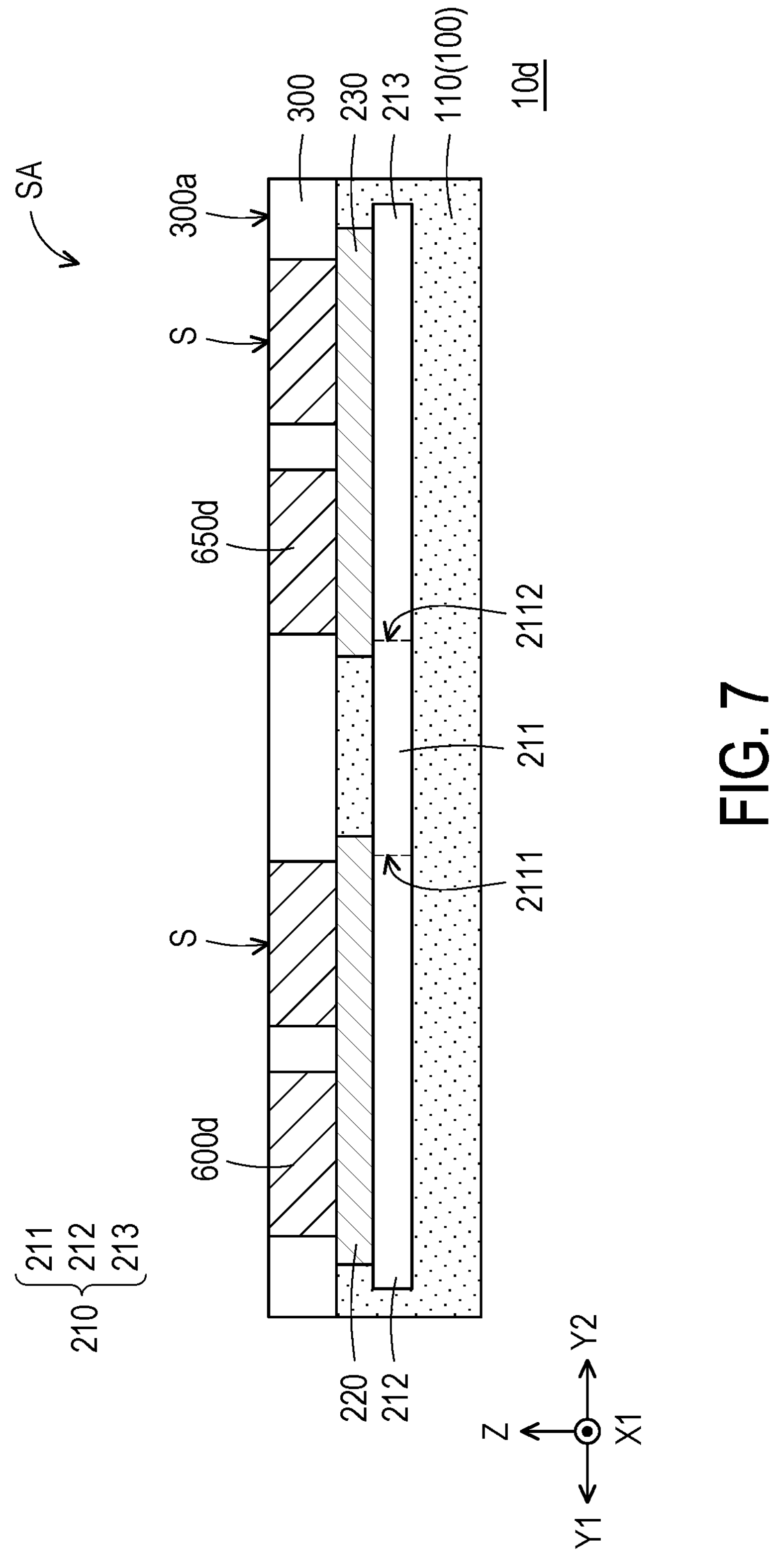
FIG. 7 is a schematic cross-sectional view of a sensing area of a flexible electronic device according to another embodiment of the present disclosure.

FIG. 7 is a schematic cross-sectional view of a sensing area of a flexible electronic device according to another embodiment of the present disclosure. Please refer to FIG. 7 and FIG. 6A both. The flexible electronic device 10*d* of this embodiment is similar to the flexible electronic device 10*c* in FIG. 6A. The only difference between them is that in the flexible electronic device 10*d* of this embodiment, the surfaces S of the signal amplification layer 600*d* and the signal amplification layer 650*d* away from the substrate 210 may be coplanar with the surface 300*a* of the second encapsulation layer 300.

Specifically, please refer to FIG. 7, the signal amplification layer 600*d* and the signal amplification layer 650*d* may penetrate the second encapsulation layer 300, and the surfaces S of the signal amplification layer 600*d* and the signal amplification layer 650*d* may be exposed outside the second encapsulation layer 300, but the disclosure is not limited thereto. In some embodiments, the surface of a part of the signal amplification layer of the plurality of signal amplification layers may be exposed outside the second encapsulation layer, and the surface of another part of the signal amplification layer of the plurality of signal amplification layers may be embedded in the second encapsulation layer.

Figure 8:
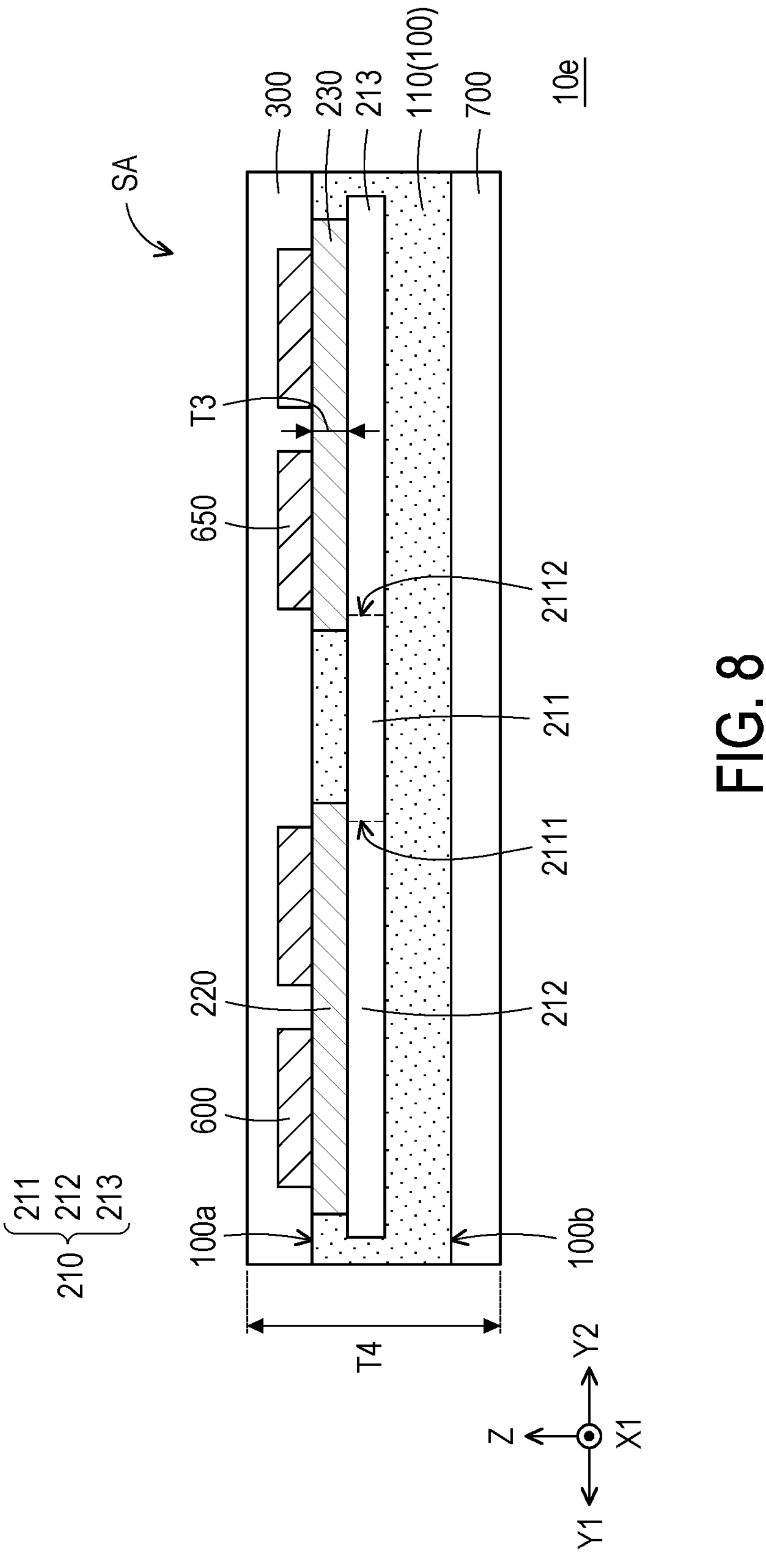
FIG. 8 is a schematic cross-sectional view of a sensing area of a flexible electronic device according to another embodiment of the present disclosure.

FIG. 8 is a schematic cross-sectional view of a sensing area of a flexible electronic device according to another embodiment of the present disclosure. Please refer to FIG. 8 and FIG. 6A both. The flexible electronic device 10*e* of this embodiment is similar to the flexible electronic device 10*c* in FIG. 6A. The only difference between them is that the flexible electronic device 10*e* of this embodiment further includes a shielding layer 700.

Specifically, referring to FIG. 8, the shielding layer 700 may be disposed under the second surface 100*b* of the first encapsulation layer 100 away from the sensing layer (i.e., the first sensing layer 220 and the second sensing layer 230). In this embodiment, the material of the shielding layer 700 may include copper, titanium, molybdenum, gold, silver, aluminum or a combination thereof, but the disclosure is not limited thereto.

In this embodiment, the shielding layer 700 may be adopted to block or reduce noise interference except for the signal (e.g., physiological signals of human body, but not limited thereto) to be sensed by the sensing layer (i.e., the first sensing layer 220 and the second sensing layer 230), thereby improving the transmission quality of the signal to be sensed.

In this embodiment, by changing the ratio of the thickness of the sensing layer (i.e., the first sensing layer 220 and the second sensing layer 230) to the thickness of the flexible electronic device 10*e*, it is possible to reduce the stress generated by the flexible electronic device 10 when the flexible electronic device 10 is stretched, twisted or bent. In this embodiment, the thickness T3 of the sensing layer (i.e., the first sensing layer 220 and the second sensing layer 230) may be, for example, 60 micrometers (μm) to 400 μm, and the thickness T4 of the flexible electronic device 10*e* may be, for example, 400 μm to 6000 μm, the ratio R2 of the thickness of the sensing layer (i.e., the first sensing layer 220 and the second sensing layer 230) to the thickness of the flexible electronic device 10*e* may be 0.01 to 1, but the disclosure is not limited thereto. For example, compared to a flexible electronic device with a ratio R2 of 0.0125, a flexible electronic device with a ratio R2 of 0.025 may have reduced stress during deformation such as stretching, torsion, or bending.

In some embodiments not shown, the shielding layer may also be disposed on the first surface 100*a* of the first encapsulation layer 100 far away from the sensing layer and on the surface of the second encapsulation layer 300 far away from the sensing layer. In some embodiments not shown, the shielding layer may also be disposed under the second surface 100*b* of the first encapsulation layer 100, on the side surface of the first encapsulation layer 100, on the surface of the second encapsulation layer 300 away from the sensing layer, and on the side surface of the second encapsulation layer 300, so that the shielding layer may completely cover the sensing layer.

In some embodiments not shown, the shielding layer may be replaced by a filtered sensing system according to user requirements to block or reduce noise interference. For example, when the sensing layer senses the physiological signals of the human body, the sensing signals may be transmitted to the filtering sensing system through contacts and transmission lines. Then, the filtering processing unit in the filtering sensing system is adopted to reduce interference from the mains power environment or filter out noise in the frequency band that interferes with physiological signals.

Figure 9:
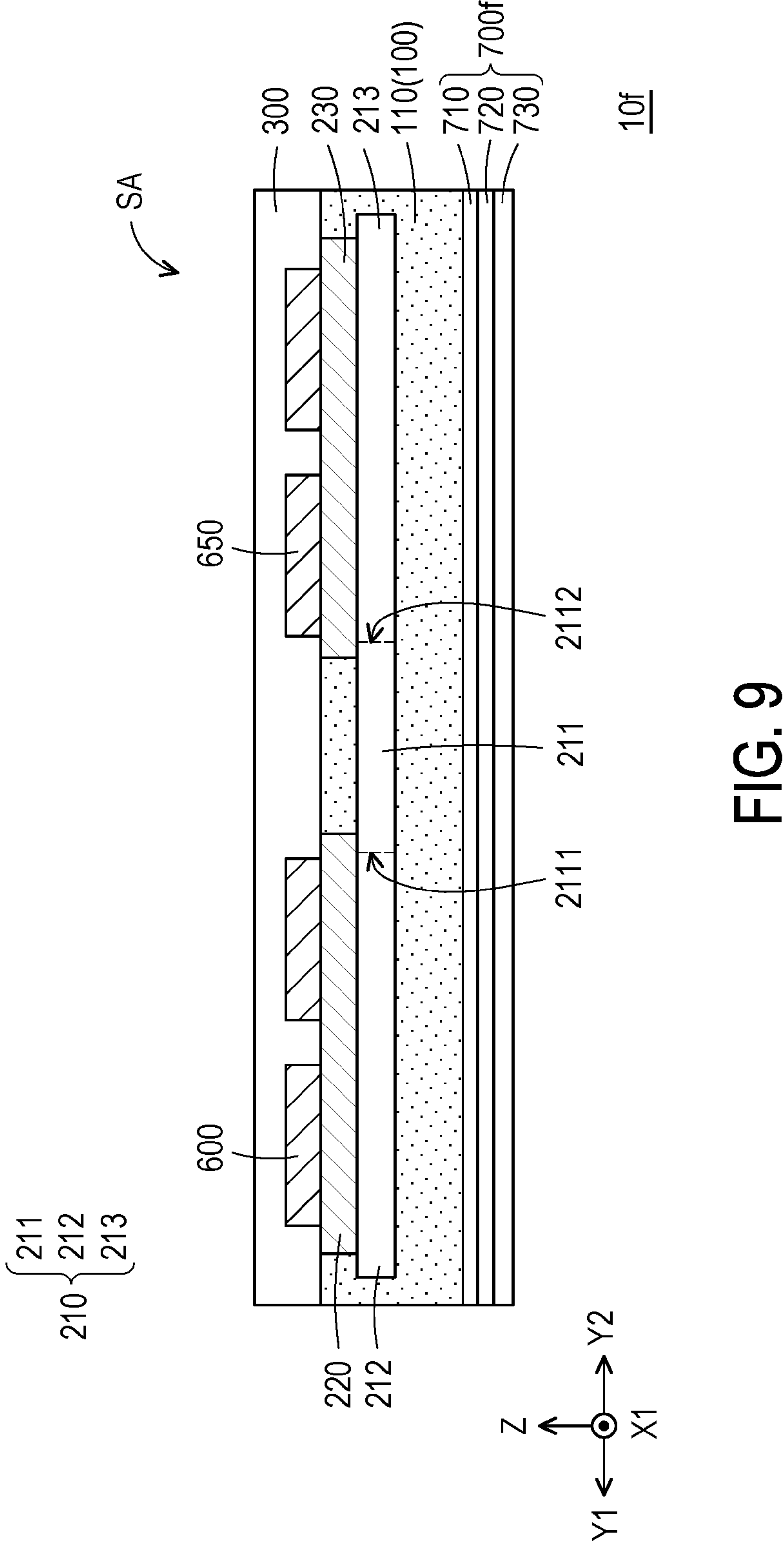
FIG. 9 is a schematic cross-sectional view of a sensing area of a flexible electronic device according to another embodiment of the present disclosure.

FIG. 9 is a schematic cross-sectional view of a sensing area of a flexible electronic device according to another embodiment of the present disclosure. Please refer to FIG. 9 and FIG. 8 both. The flexible electronic device 10*f* of this embodiment is similar to the flexible electronic device 10*e* in FIG. 8. The only difference between them is that the shielding layer 700*f* of the flexible electronic device 10*f* of this embodiment has a multi-layer structure, which is different from the single-layer shielding layer 700 in the flexible electronic device 10*e* of FIG. 8.

Specifically, please refer to FIG. 9. The shielding layer 700*f* includes a first layer 710, a second layer 720, and a third layer 730 in sequence. The second layer 720 is disposed between the first layer 710 and the third layer 730. In this embodiment, the materials of the first layer 710 and the third layer 730 may include copper, titanium, molybdenum, gold, silver, aluminum or a combination thereof, and the material of the second layer 720 may include polydimethylsiloxane (PDMS), trimethylsiloxane (—O—Si$(CH_3)_3$), hexamethyldisiloxane (HMDSO), fabric, leather, or silicone, but the disclosure is not limited thereto.

In this embodiment, the shielding layer 700*f* may be used to filter and shield high-frequency noise, so that the noise may be reflected away from the internal components (such as the sensing layer) of the flexible electronic device 10*f*, thereby enhancing the transmission quality of the signal to be sensed.

In summary, in the flexible electronic device according to an embodiment of the present disclosure, since the deformation amount of the second region of the first encapsulation layer may be greater than the deformation amount of the first region and the deformation amount of the third region, when subjected to an external force, the external force may be withstand by increasing the deformation amount of the second region, and limiting the deformation amount of the first region and the third region to protect the sensing structure disposed in the first region and the system component disposed in the third region. In this embodiment, through the arrangement of the first groove and the second groove, the stress generated by the flexible electronic device during deformation such as stretching, twisting or bending may be reduced and the overall amount of stress may be increased, so that the average allowable stretch amount of the flexible electronic device 10 may be increased by more than 20%. Moreover, the flexible electronic device may be adapted to stretching, twisting, bending and other deformations to avoid damage or failure during configuration or use, thereby improving the service life, yield or reliability of the flexible electronic device. In this embodiment, through the arrangement of the signal amplification layer, the amount of electrical coupling may be increased, thereby improving the intensity of the signal transmitted or received by the flexible electronic device.

Although the present disclosure has been disclosed in the above embodiments, it is not intended to limit the present disclosure. Anyone with ordinary knowledge in the technical field may make some modifications and refinement without departing from the spirit and scope of the present disclosure, so the protection scope of the present disclosure shall be determined by the appended claims.

What is claimed is:

1. A flexible electronic device, comprising:
- a first encapsulation layer; and
- a sensing structure disposed on the first encapsulation layer and comprising:
  - a substrate comprising:
    - a main body having a first side and a second side opposite to each other;
    - a plurality of first branches connecting the first side; and
    - a plurality of second branches connecting the second side;
  - a plurality of first sensing layers disposed on the plurality of first branches;
  - a plurality of second sensing layers disposed on the plurality of second branches;
  - a first groove disposed between the plurality of first branches; and
  - a second groove disposed between the plurality of second branches.

2. The flexible electronic device according to claim 1, wherein a first extension direction of the plurality of first branches is substantially parallel to a second extension direction of the plurality of second branches, and a third extension direction of the main body is substantially perpendicular to the first extension direction and the second extension direction.

3. The flexible electronic device according to claim 1, wherein the main body and the plurality of first branches are arranged in a comb shape.

4. The flexible electronic device according to claim 1, wherein the plurality of first sensing layers are disposed corresponding to edges of the plurality of first branches, and the plurality of second sensing layers are disposed corresponding to edges of the plurality of second branches.

5. The flexible electronic device according to claim 1, wherein the plurality of first sensing layers are electrically separated from the plurality of second sensing layers.

6. The flexible electronic device according to claim 1, wherein the first encapsulation layer has a first area, the substrate has a second area, and the second area is 10% to 97% of the first area.

* * * * *